United States Patent [19]
Jiang et al.

[11] Patent Number: 5,847,046
[45] Date of Patent: Dec. 8, 1998

[54] BIODEGRADABLE BONE CEMENT

[75] Inventors: Ying Jiang, North Haven; Mark Roby, Killingworth, both of Conn.

[73] Assignee: United States Surgical Corporation, Norwalk, Conn.

[21] Appl. No.: 815,613

[22] Filed: Mar. 12, 1997

[51] Int. Cl.$^6$ .......... C09J 133/04; C09J 133/02; C09J 167/06; C09J 4/00
[52] U.S. Cl. .......... 524/42; 424/426; 514/772.3; 514/772.4; 514/772.6; 523/116; 523/118; 525/48; 525/411; 525/412; 525/450
[58] Field of Search .......... 523/116, 118; 514/772.3, 772.4, 772.6; 424/426, 78.18; 525/42, 48, 411, 412, 450

[56] References Cited

U.S. PATENT DOCUMENTS

| | | | |
|---|---|---|---|
| 2,844,559 | 7/1958 | Parker | 524/320 |
| 3,838,093 | 9/1974 | Owston | 524/317 |
| 4,093,576 | 6/1978 | deWijn | 523/114 |
| 4,341,691 | 7/1982 | Anuta | 523/116 |
| 4,373,217 | 2/1983 | Draenert | 623/16 |
| 4,842,603 | 6/1989 | Draenert | 623/16 |
| 4,898,734 | 2/1990 | Mathiowitz et al. | 424/426 |
| 4,969,906 | 11/1990 | Kronman | 623/16 |
| 4,997,446 | 3/1991 | Thoma | 623/16 |
| 5,216,050 | 6/1993 | Sinclair | 524/108 |
| 5,334,626 | 8/1994 | Lin | 523/116 |
| 5,336,699 | 8/1994 | Cooke et al. | 523/115 |
| 5,607,686 | 3/1997 | Totakura et al. | 424/426 |

FOREIGN PATENT DOCUMENTS

| | | |
|---|---|---|
| 0522569 | 1/1993 | European Pat. Off. |
| 2917037 | 4/1980 | Germany. |
| 8700419 | 1/1987 | WIPO. |

OTHER PUBLICATIONS

Bone Cement—Dough Type, L.V.C. Bone Cement—Low viscosity; Zimmer, Inc.; Warsaw, Indiana; pp. 1–8; Revised Aug. 1992.

*Primary Examiner*—Peter A. Szekely

[57] ABSTRACT

A surgical bonding material includes a continuous phase and a discontinuous phase. The continuous phase is formed from a polymerizable liquid. The discontinuous phase includes particles of bioabsorbable polymer. The bonding material may be partially or completely bioabsorbable.

20 Claims, No Drawings

BIODEGRADABLE BONE CEMENT

BACKGROUND

1. Technical Field

The present disclosure relates to bonding materials suitable for use in medicine. More particularly, the bonding material can be utilized as fully or partially degradable cement for prosthesis fixation.

2. Background of Related Art

Various materials have been described for use in repairing hard tissue such as bone or for bonding prosthetics to hard tissue. Such materials may incorporate acrylates which polymerize in situ to form a graft or cement bond. For example, U.S. Pat. No. 4,341,691 is directed to a low viscosity bone cement which, as described therein, consists of a mixture of a liquid monomer component and a polymer powder component. The liquid monomer component is methyl methacrylate monomer, N, N-dimethyl-p-toluidine and hydroquinone. The polymer powder is polymethylmethacrylate, benzoyl peroxide and optionally barium sulfate.

U.S. Pat. No. 5,334,626 is directed to a bone cement composition and method of its manufacture. As described therein, bone cement consists of a liquid monomer component and a dry component including polymer beads. The beads contain a polymerization initiator such as benzoyl peroxide. When the dry component is mixed with the liquid monomer component, the monomer is said to partially dissolve the beads allowing benzoyl peroxide to become available to the monomer. The benzoyl peroxide decomposes in the presence of N,N-dimethyl-p-toluidine into free radicals which act as polymerization initiators for the monomer, and polymer chains begin forming from the beads outwardly. As polymerization continues, the composition grows more viscous until it hardens. The polymerization initiator may be placed on the surface of the bead to cause polymerization to begin upon mixing of dry and liquid components. In one aspect, the bead is described as layered to control the release of the initiator to affect rheological properties.

Certain materials have been utilized because they are said to allow in-growth of bone after implantation in the body. As described in U.S. Pat. No. 4,373,217, certain acrylates used in bone replacement, bone bonding and prosthesis anchoring are not resorbed in the body and are enveloped by the body's own tissue. Biomechanical overstressing is said to occur at the relatively small boundary surface area of implant/body which leads to a loosening of the implant. Thus, implants are described therein having a porous structure which allow such implants to be permeated by a growth of body tissue. Calcium triphosphate of a defined particle size is mixed with cements based on polyacrylates. In one aspect tricalcium phosphate is added to monomer which triggers polymerization. After polymerization, tricalcium phosphate particles are said to be resorbed in such a way as to form channels which allow bone growth. However, as described in U.S. Pat. No. 4,842,603, particles of filler such as tricalcium phosphate can be the starting point of disintegration of the implant since particles of tricalcium phosphate do not participate in elastic movement of the acrylate polymer. Stress situations are said to arise at the incorporated particles which, in the long term, destroy the structure of the polymer. Spherical particles of tricalcium phosphate are proposed therein to solve the problem of destruction.

EP 0 522 569 is directed to a composition for effecting bone repair which includes biocompatable particles dispersed in a matrix. As described therein, the matrix is selected from the group consisting of cellulose ether, collagen, hyaluronic acid and certain salts and/or derivatives of hyaluronic acid. The biocompatible particles which are dispersed in the matrix can be formed from either bioabsorbable material or nonbioabsorbable material. Suitable bioabsorbable material can be derived from, e.g., polyglycolic acid, glycolide, lactic acid, lactide and others. When wet, the composition forms a moldable, semi-solid mass which can be suitably worked for implantation into bone. The composition will remain in moldable or semisolid form as long as not permitted to dry out.

There is a continuing need for surgical implantation materials which bond and/or augment hard tissue and which maximize workability, bonding strength and durability after implantation into the body.

SUMMARY

A biocompatable implantable bonding material is provided which includes a mixture including a continuous phase and a discontinuous phase, the continuous phase formed from polymerizable liquid and the discontinuous phase including particles of bioabsorbable polymer. Upon mixing of the continuous phase with the discontinuous phase, the continuous phase undergoes polymerization and cures. In one aspect, the continuous phase is formed from unsaturated polyester. In another aspect, the continuous phase is formed from acrylic acid monomer, methacrylic acid monomer, acrylate monomer, methacrylate monomer or combinations thereof. In one aspect, the discontinuous phase includes free radical catalyst and the continuous phase includes free radical catalyst activator.

A kit for biocompatible implantable bonding material is provided which includes at least first and second components. The first component includes particles of bioabsorbable polymer and free radical catalyst. The second component includes unsaturated polyester, vinyl monomer and catalyst activator.

A kit for biocompatible implantable bonding material is provided which includes at least first and second components. The first component includes particles of bioabsorbable polymer and free radical catalyst. The second component includes liquid monomer which is acrylic acid monomer, methacrylic acid monomer, acrylate monomer, methacrylate monomer or combinations thereof, and catalyst activator.

A method of manufacturing a biocompatable bonding material is provided which includes providing polymerizable liquid, providing particles of biobabsorbable polymer, mixing polymerizable liquid with particles of bioabsorbable polymer and allowing polymerizable liquid to polymerize. In one aspect the polymerizable liquid is unsaturated polyester and vinyl monomer. In another aspect, polymerizable liquid is acrylic acid monomer, methacrylic acid monomer, acrylate monomer, methacrylate monomer or combinations thereof.

DETAILED DESCRIPTION OF THE PREFERRED EMBODIMENTS

Surgical bonding material containing particles of bioabsorbable polymer in a discontinuous phase and a polymerizable liquid in a continuous phase is provided. As a result of polymerization, the continuous phase cures and becomes a polymeric network containing bioabsorbable particles in the discontinuous phase. The bioabsorbable polymers degrade by hydrolysis and provide regions suitable for bone in-growth into the continuous phase. In contrast to particles of tricalcium phosphate used as a vehicle to promote bone in-growth which, as indicated in U.S. Pat. No. 4,842,603, can be the starting point of disintegration of an implant, particles of bioabsorbable polymers as described herein participate in elastic movement of the implant and do not become the starting point for disintegration of the implant. Indeed, as described below, polymeric chains which make up the continuous phase actually extend from and/or surround the polymeric bioabsorbable particles as a result of the polymerization processes described herein. Moreover, since the modulus of elasticity and tensile strength of various bioabsorbable polymers are well-known, they can be tailored to be as elastic, more elastic or less elastic than the polymers of the continuous phase, depending on the requirements of the end product. Furthermore, it is also known that by adjusting components and manufacturing processes of bioabsorbable polymers, degradation time can be increased or decreased to coincide with tissue in-growth or other requirements of the surgical setting.

Bioabsorbable polymers which are incorporated into the discontinuous phase are well-known. For example, bioabsorbable polymers may be derived from glycolic acid, glycolide, lactic acid, lactide, dioxanone, epsilon-caprolactone, trimethylene carbonate, hydroxybutyrate, hydroxyvalerate, polyanhydrides, and homopolymers and copolymers thereof and are described in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,060,089; 4,137,921; 4,157,437; 4,234,775; 4,237,920; 4,300,565; 4,523,591; 4,920,203; 5,152,781; 5,123,912; 5,312,437; U.K. Patent No. 799,291; D. K. Gliding et al., "Biodegradable polymers for use in surgery—polyglycolic/poly(lactic acid) homo-and co-polymers": 1, *Polymer*, Volume 20, pages 1459–1464 (1979), and D. F. Williams (ed.), *Biocompatability of Clinical Implant Materials*, Vol. II, ch. 9: "Biodegradable Polymers" (1981). All the foregoing documents are herein incorporated by reference.

Hard phase forming monomers, such as copolymers derived from glycolide and lactide are especially preferred for use herein; see for example U.S. Pat. Nos. 4,523,591; 4,744,365; 4,839,130; 4,844,854; 5,019,093; 5,124,103.

Manufacture of particles from larger mass objects is well-known to those with skill in the art. For example, mechanical grinding or milling, solvent precipitation, dispersion and spray atomization of solutions or slurries are well-known techniques which can be utilized to form particles of bioabsorbable polymers. See, e.g, U.S. Pat. Nos. 5,143,682 and 5,342,557, both incorporated herein by reference. Foamed bioabsorbable particles as described in U.S. Pat. No. 5,102,983, incorporated herein by reference, may also be utilized.

Particles of bioabsorbable polymer can be made to degrade at different rates by controlling content of particular polymers and by varying manufacturing processes of particular polymers. For example, it is known that bioabsorbable compositions made of lactide degrade faster than bioabsorbable compositions made of glycolide. By adjusting the ratio of lactide and glycolide in bioabsorbable polymers, the rate of hydrolysis and degradation can be increased or decreased. Use of foam bioabsorbable particles contributes to faster degradation times when desired. In this manner, the bioabsorbtion rate of the particles can be controlled and made to coincide with in-growth of tissue or to coincide with any suitable predetermined time frame.

Polymeric bioabsorbable particles may be of varied size and shape. For example, such particles can be utilized in the form of beads having average particle size (diameter) ranging from about 0.1 mm to about 3 mm and preferably from about 0.2 mm to about 1.0 mm.

The continuous phase substantially surrounds the particles which make up the discontinuous phase. The continuous phase may be absorbable, as in the case of certain polyesters described below, or non-absorbable as the in the case of acrylic polymers, methacrylic polymers, acrylates and methacrylates as described below. When both the continuous phase and discontinuous phase are absorbable, the present surgical bonding material is fully absorbable. When the continuous phase is non-absorbable and the discontinuous phase is absorbable, the present surgical bonding material is partially absorbable. By adjusting the rate of hydrolysis of the bioabsorbable particles in the discontinuous phase, the discontinuous phase can degrade faster than the absorbable continuous phase, thus providing regions for tissue in-growth within or around the continuous phase. Polymeric bioabsorbable particles located on the surface of a partially absorbable implant herein degrade to provide regions for tissue anchoring at the surface of the implant. Polymeric bioabsorbable particles which are located below the surface of the implant, within the continuous phase, and which contact surface located or other hydrolyzing polymeric bioabsorbable particles will in turn hydrolyze and degrade on contact with body fluids, thus creating channels suitable for in-growth of tissue within the continuous phase.

In one aspect, the continuous phase is formed from a polymerizable liquid monomer of acrylic acid, methacrylic acid, acrylate and/or methacrylate thereof. Manufacture of acrylic acid monomers, methacrylic acid monomers, acrylate monomers and methacrylate monomers, is well-known. See, e.g., Encyclopedia of Polymer Science, 2d ed., John Wiley & Sons, Vol. 1, pp.213–219 and pp. 247–251 (1985), herein incorporated by reference. As used herein acrylate or methacrylate generally includes esters thereof. Methods of polymerizing or copolymerizing acrylic acid monomers, methacrylic acid monomers, or acrylate monomers and methacrylate monomers are also well-known. Free radical catalysts, also known as polymerization initiators, combined with catalyst activators, also known as polymerization accelerators, cause the monomers to polymerize at relatively low temperatures such as body temperature at 37° C. The free radical polymerization of acrylic acid, methacrylic acid, acrylate and methacrylate monomers follows a classical chain mechanism which involves head to tail growth of the polymeric free radical by attack on the double bond of the monomer which is described, e.g., in the *Encyclopedia of Polymer Science*, supra, at pp. 266–269 herein incorporated by reference. Although methyl methacrylate monomer is preferred herein, all the aforementioned monomers are readily copolymerizable with each other and many other monomers. Polymers which are all acrylic tend to be soft and tacky while polymers which are all methacrylic tend to be hard and brittle. Copolymerization of the aforesaid monomers allows adjustment of properties as desired.

It is contemplated that prior to combining the continuous phase and discontinuous phase, the catalyst may be placed in one phase and activator placed in the other phase such that, upon mixing, polymerization of the monomer begins. For example, the bioabsorbable polymeric particles are soaked in catalyst to cause the particles to absorb some of the catalyst and to deposit some catalyst on the surface of the particles. The activator is mixed with the monomer. In this manner, when the liquid monomer is mixed with the polymeric bioabsorbable particles, the catalyst decomposes into free radicals in the presence of activator which causes polymerization of the monomer and, since the activated catalyst is located in, on or proximate to the particles, polymer chains form outwardly from the particles. As a result, the liquid monomer is transformed into a rigid plastic state and a stable structure is created in which the discontinuous phase is dispersed within the continuous phase.

In another aspect, the continuous phase is formed from an unsaturated polyester made by esterification of a glycol with an unsaturated acid. Free radical catalysts initiate cross-linking reactions involving double bonds in the unsaturated polyester and an unsaturated correactant monomer such as vinyl monomer, which transforms the low viscosity unsaturated polyester into a rigid plastic state.

Preferred bioabsorbable polyesters are formed from fumaric acid. The polyester is degraded by chemical attack by small polar molecules such as water on the polar ester groups of the polyester. Fumaric acid is a biocompatable dibasic acid which is esterified with an alkylene glycol such as propylene glycol, ethylene glycol and diethylene glycol to prepare a liquid polyester. Methods of preparing such liquid polyesters are well known, i.e., see *Encyclopedia of Polymer Science*, supra, at pp. 259–268, herein incorporated by reference.

The liquid polyester is transformed into a rigid plastic state by cross-linking with unsaturated monomers such as vinyl monomers including, e.g., styrene, diallyl phthalate, triallyl cyanurate and diallyl diglycol carbonate. Such cross-linking is initiated by free radical catalysts which, in a manner similar to that described above, are activated by an activator. The catalyst is decomposed by the activator to yield free radicals which cause cross-linking to proceed, thus transforming the liquid polyester into a soft rubbery gel. As the reaction continues, the soft rubber is transformed into a rigid plastic.

The polymeric bioabsorbable particles are soaked with catalyst to cause the particles to absorb some of the catalyst and to deposit some catalyst on the surface of the particles. The activator is mixed with the liquid polyester/vinyl monomer. In this manner, when the liquid polyester is mixed with the polymeric bioabsorbable particles, the catalyst decomposes into free radicals in the presence of activator which causes cross-linking of the polyester and vinyl monomer. Since the cross-linking occurs in or around the particles, the particles are bound in a cross-linked three dimensional polymeric network.

Free radical catalysts are well known. Examples of free radical catalysts suitable for use herein include but are not limited to azo catalysts such as azobisbutyronitrile and 4,4'-azo-4-cyanopentanoic acid, peroxy compounds such as benzoyl peroxide and di-t-butyl peroxide, peresters such as t-butyl peresters, such as t-butyl perbenzoate peroxalates, persulfates such as potassium persulfate and hydroperoxides. Peroxy compounds are preferred catalysts, including compounds such as organic peroxides, e.g., diacryl peroxides and peroxyesters, peroxydicarbonates, diperoxyketals and dialkyl peroxides. Specific peroxy compounds include diacyl peroxides, acetyl alkylsufonyl peroxides, dialkyl peroxy dicarbonates, tert-alkyl peroxyesters, OO-tert-alkyl O-alkyl monoperoxycarbonates, di (tert-alkylperoxy) ketals, di (tert-alkyl) peroxides, tert-alkyl hydroperoxides and ketone peroxides. Preferred peroxides include the aryl and diaryl peroxides such as benzoyl peroxide, dibenzoyl peroxide, 2,4-dichlorobenzoyl peroxide and di (2,4-dichloro benzoyl) peroxide, acetyl peroxide and diacetyl peroxide, lauroyl peroxide and dilauroyl peroxide, decanoyl peroxide and didecanoyl peroxide, isononanoyl peroxide and diisononanoyl peroxide and succinic acid peroxide. Other examples of suitable peroxide initiatives can be found in *Encyclopedia of Polymer Science and Engineering*, Volume 11, pp. 1–21, John Wiley & Sons, New York (1988), incorporated herein by reference. Generally the amount of free radical catalyst that can be incorporated to initiate polymerization is about 0.01% by weight to about 0.05% by weight of the total bonding material.

Catalyst activators are also well known. Examples of catalyst activator suitable for use herein include but are not limited to amine activators like tertiary amines such as triethylamine, pyridine, vinylpyridine, imidazoles and picolines. A preferred tertiary amine activator is N, N-dimethyl-p-toluidine. The tertiary amine activator is incorporated in the bonding material in an amount ranging from about 0.001% to about 0.01% by weight of the total composition.

In one aspect, a kit is provided which includes at least two components. For example, the components forming the biodegradable bone cement may be packaged in respective containers, i.e., as a first component, the polymeric bioabsorbable particles soaked with free radical catalyst can be packaged in one container. As a second component, polymerizable liquid is packaged in another container, with or without catalyst activator present therein.

Polymerization of the polymerizable liquid to form the continuous phase begins upon mixing of all components together. As a result, viscosity of the resulting blend increases such that after about five minutes, a semisolid composition of appropriate thickness and consistency will be reached. The resulting composition is then applied onto a prosthesis or hard tissue with an appropriate instrument, e.g., a surgical spatula. The prosthesis is then inserted in place into a bone defect site and retained until an appropriate bond is formed. The prosthesis can be optionally retained in place by other fixation means, e.g., surgical clips, set screws, etc. After curing is complete and the bonding material has set, if fully absorbable, the surgical bonding material will be gradually absorbed over time. Partially absorbable bonding material will be partially absorbed over time. New tissue in-growth will gradually replace the portion of the hardened bonding material that is absorbed. Hard tissue in-growth will effect a firm union between the implanted prosthesis and underlying bone tissue, securely fixing the prosthesis in position.

The following examples are included to illustrate certain aspects and should not be construed as limiting the disclosure herein.

EXAMPLE I 10 g of bioabsorable polymer particles (0.2–0.4 mm diameter) are suspended in 10 ml ether solution which contains 0.5 mg of free radical catalyst benzoyl peroxide. The suspension is stirred at room temperature for 30 minutes and ether is evaporated using a rota-vap. The catalyst coated particles are then dried in vacuum for 12 hours. The dried particles are packed under nitrogen gas in a first glass vial and are ready for application.

4g of purified methymethacrylate is mixed with 0.75 mg N,N-dimethyl-p-toluidine as activator. The solution is stirred at room temperature for 20 minutes. Nitrogen gas is bubbled through for five minutes and the mixture is then packed under nitrogen gas in a second glass vial. In application, the materials from the two vials described above are combined and mixed well with a spatula in a glass dish. After three minutes, the mixture becomes warm and at five minutes it is applied to the site and cured for 20 minutes. A hard cement-like material is obtained.

EXAMPLE II 10 g of bioabsorable polymer particles (0.2–0.4 mm diameter) are suspended in 10 ml ether solution which contains 0.5 mg of free radical catalyst benzoyl peroxide. The suspension is stirred at room temperature for 30 minutes and ether is evaporated using a rota-vap. The catalyst coated particles are then dried in vacuum for 12 hours. The dried particles are packed under nitrogen gas in a first glass vial and are ready for application.

5 g of poly (diethylene glycol fumarate) is mixed with 1 mg of N,N-dimethyl-p-toluidine. After flushing with nitrogen for 20 minutes, the mixture is packaged under nitrogen in a glass vial. In application, the materials from the two vials described above are combined and mixed well with a spatula in a glass dish. After three minutes, the mixture becomes warm and at five minutes it is applied to the site and cured for 20 minutes. A hard cement-like material is obtained.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A biocompatable implantable bonding material comprising a mixture including a continuous phase and a discontinuous phase, the continuous phase formed from polymerizable liquid, the discontinuous phase including of particles of bioabsorbable polymer whereby upon mixing of the continuous phase and the discontinuous phase, the polymerizable liquid undergoes polymerization.

2. A biocompatable implantable bonding material according to claim 1 wherein particles of bioabsorbable polymer include free radical catalyst and polymerizable liquid includes a catalyst activator.

3. A biocompatable implantable bonding material according to claim 1 wherein polymerizable liquid includes unsaturated polyester and vinyl monomer.

4. A biocompatable implantable bonding material according to claim 3 wherein the unsaturated polyester is polyalkylene glycol fumarate.

5. A biocompatable implantable bonding material according to claim 1 wherein the continuous phase is a polymer formed from monomer selected from the group consisting of acrylic acid monomer, methacrylic acid monomer, acrylate monomer, methacrylate monomer and combinations thereof.

6. A biocompatable implantable bonding material according to claim 1 wherein bioabsorbable polymer is formed from a moiety selected from the group consisting of glycolic acid, glycolide, lactic acid, lactide, dioxanone, epsilon-caprolactone, trimethylene carbonate, hydroxybutyrate, hydroxyvalerate, polyanhydride and combinations thereof.

7. A kit for biocompatable implantable bonding material comprising at least first and second components, the first component including particles of bioabsorbable polymer and free radical catalyst, the second component including unsaturated polyester, vinyl monomer and catalyst activator.

8. A kit for biocompatable implantable bonding material according to claim 7 wherein bioabsorbable polymer is formed from a moiety selected from the group consisting of glycolic acid, glycolide, lactic acid, lactide, dioxanone, epsilon-caprolactone, trimethylene carbonate, hydroxybutyrate, hydroxyvalerate, polyanhydride and combinations thereof.

9. A kit for biocompatable implantable bonding material according to claim 7 wherein unsaturated polyester is polyalkylene glycol fumarate.

10. A kit for biocompatable implantable bonding material according to claim 7 wherein vinyl monomer is styrene.

11. A kit for biocompatable implantable bonding material comprising at least first and second components, the first component including particles of bioabsorbable polymer and free radical catalyst, the second component including liquid monomer selected from the group consisting of acrylic acid monomer, methacrylic acid monomer, acrylate monomer, methacrylate monomer and combinations thereof, and catalyst activator.

12. A kit for biocompatable implantable bonding material according to claim 11 wherein bioabsorbable polymer is formed from a moiety selected from the group consisting of glycolic acid, glycolide, lactic acid, lactide, dioxanone, epsilon-caprolactone, trimethylene carbonate, hydroxybutyrate, hydroxyvalerate, polyanhydride and combinations thereof.

13. A kit for biocompatable implantable bonding material according to claim 11 wherein methacrylate liquid monomer is methylmethacrylate.

14. A method of manufacturing biocompatable bonding material comprising:
    providing polymerizable liquid;
    providing particles of bioabsorbable polymer;
    mixing particles of bioabsorbable polymer with polymerizable liquid;
    allowing polymerizable liquid to polymerize.

15. A method of manufacturing biocompatable implantable bonding material according to claim 14 wherein particles of bioabsorbable polymer include free radical catalyst and polymerizable liquid includes catalyst activator.

16. A method of manufacturing biocompatable implantable bonding material according to claim 14 wherein polymerizable liquid includes unsaturated polyester and vinyl monomer.

17. A method of manufacturing biocompatable implantable bonding material according to claim 16 wherein unsaturated polyester is formed from polyalkylene glycol and fumaric acid.

18. A method of manufacturing biocompatable implantable bonding material according to claim 16 wherein vinyl monomer is styrene.

19. A method of manufacturing a biocompatable implantable bonding material according to claim 14 wherein polymerizable liquid includes a monomer selected from the group consisting of acrylate monomer, methacrylate monomer acrylic acid monomer, methacrylic acid monomer and combinations thereof.

20. A method of manufacturing biocompatable implantable bonding material according to claim 14 wherein bioabsorbable polymer is formed from a moiety selected from the group consisting of glycolic acid, glycolide, lactic acid, lactide, dioxanone, epsilon-caprolactone, trimethylene carbonate, hydroxybutyrate, hydroxyvalerate, polyanhydride and combinations thereof.

* * * * *